United States Patent [19]

Bolduc

[11] Patent Number: 4,547,188

[45] Date of Patent: Oct. 15, 1985

[54] MATERIAL DISPENSING APPARATUS

[75] Inventor: Lee R. Bolduc, Raleigh, N.C.

[73] Assignee: BioNexus, Inc., Raleigh, N.C.

[21] Appl. No.: 551,058

[22] Filed: Nov. 14, 1983

[51] Int. Cl.[4] .............................................. A61M 1/00
[52] U.S. Cl. .......................................... 604/55; 604/96
[58] Field of Search .................. 604/96, 97, 98, 99, 604/54, 53, 55

[56] References Cited

U.S. PATENT DOCUMENTS

| | | | |
|---|---|---|---|
| 4,109,654 | 8/1978 | Bolduc et al. | 604/55 |
| 4,182,328 | 1/1980 | Bolduc et al. | 604/55 |

*Primary Examiner*—John D. Yasko
*Attorney, Agent, or Firm*—Vidas & Arrett

[57] ABSTRACT

A dispensing apparatus for placing a settable, fluid-like material in the uterine cavity and moving the material from the uterine cavity into the Fallopian tubes of a female. An elongated disposable dispensing probe carries an expandable member, and a housing connected to the probe has a piston and cylinder structure and a container for storing the material. Material and expansion drive mechanisms are connected to an actuator selectively controlled by an operator. By operating the actuator or control means, the operator causes the material to be dispensed into the uterine cavity while at the same time sealing the cervical entrance to the cavity, and causing the expansion means to expand, substantially filling the uterine cavity and forcing the dispensed material into the canals of the Fallopian tubes. By maintaining actuation of the control means, the operator causes the expandable member to substantially seal the isthmus, that is, the entrance from the uterine cavity into the Fallopian tubes, thus preventing the dispensed material from flowing out of the Fallopian tubes and causing it to remain in the tubes for a period of time sufficient for it to "set-up".

17 Claims, 6 Drawing Figures

U.S. Patent    Oct. 15, 1985    4,547,188
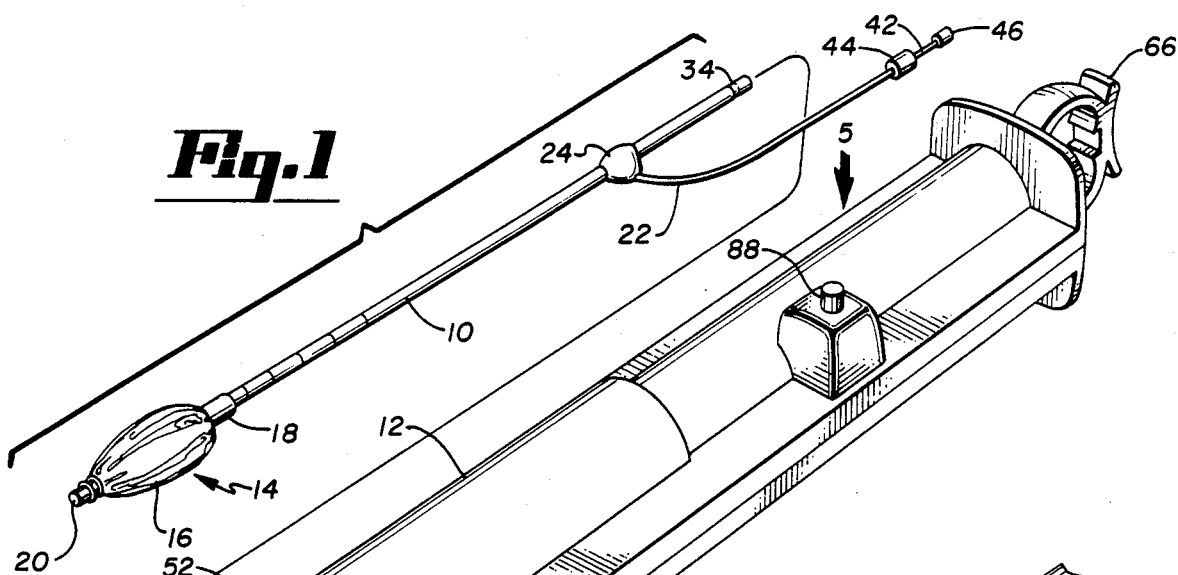
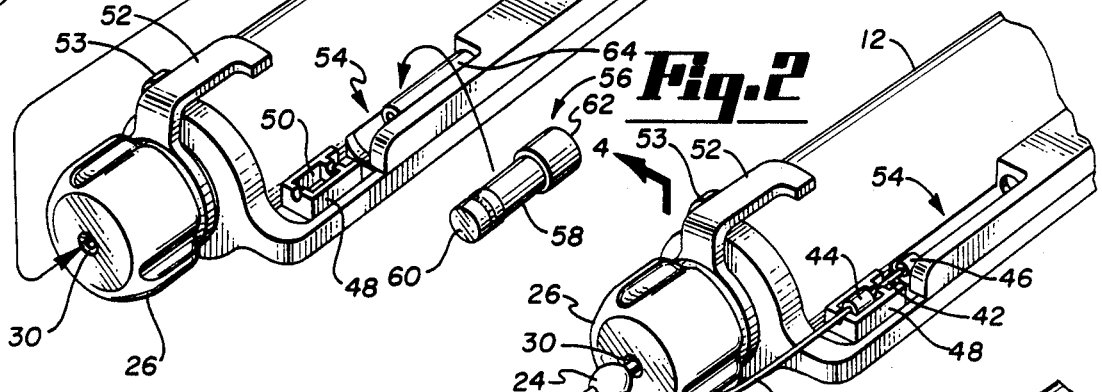
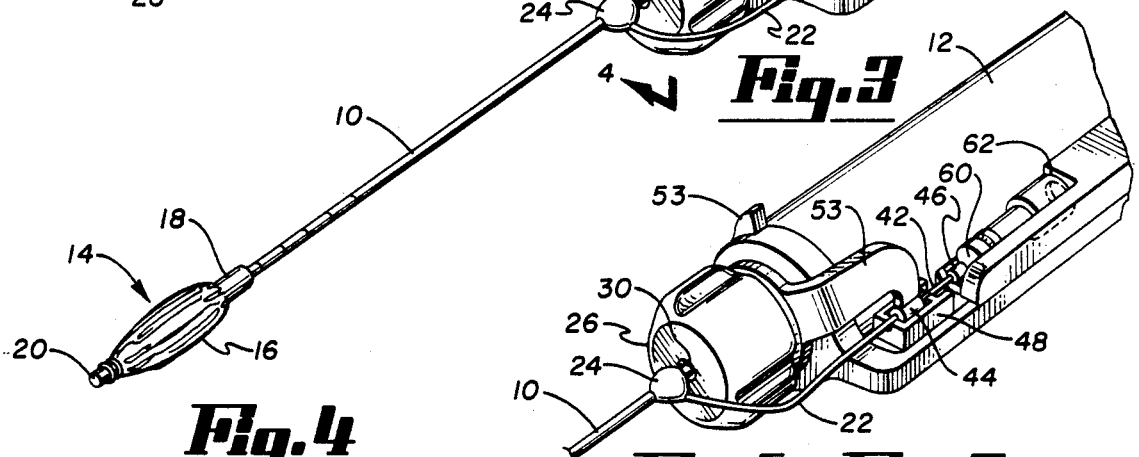
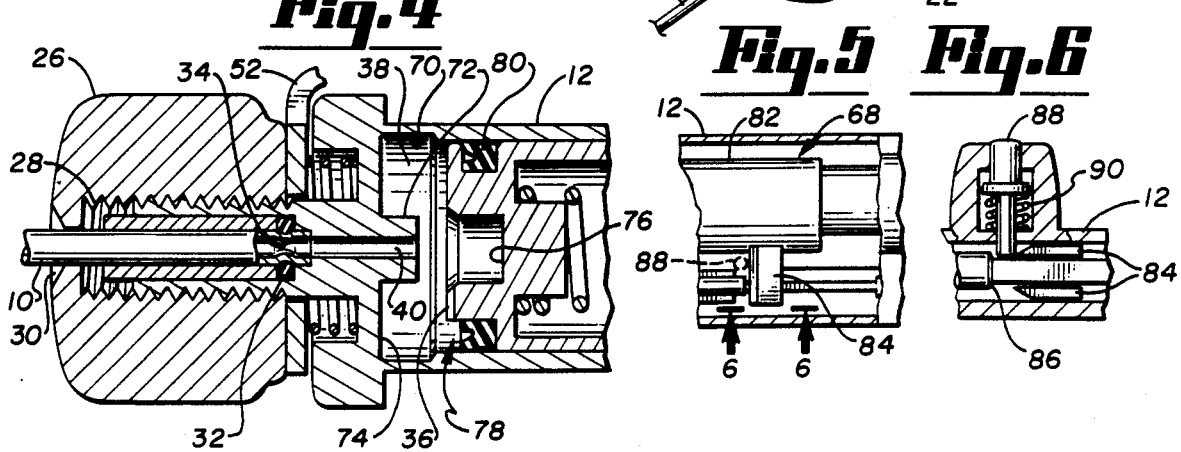

MATERIAL DISPENSING APPARATUS

BACKGROUND OF THE INVENTION

Apparatus for dispensing material into the Fallopian tubes of a female through non-surgical procedures have been described in a plurality of patents issued jointly to the inventor of this invention including but not limited to U.S. Pat. No. 3,875,939, entitled SINGLE STROKE DISPENSING METHOD, issued Apr. 8, 1975; U.S. Pat. No. 4,109,654, entitled SINGLE STROKE DISPENSING APPARATUS, ISSUED Aug. 29, 1978; U.S. Pat. No. 4,119,098, entitled IMPROVED MATERIAL DISPENSING APPARATUS, issued Oct. 10, 1978; U.S. Pat. No. 4,182,328, entitled DISPENSING INSTRUMENT AND METHOD, issued Jan. 8, 1980 and U.S. Pat. No. 4,207,891, entitled DISPENSING INSTRUMENT WITH SUPPORTED BALLOON, issued June 17, 1980.

Through the use of such dispensing apparatus, "settable" liquid or fluid-like material is injected into the Fallopian tubes to occlude them. The materials used for this purpose are generally fast setting polymerizable materials and are often sensitive to moisture. Therefore, they quickly "set-up" in the uterine cavity if not rapidly forced into the Fallopian tubes. This rapid movement of the materials is accomplished with the subject apparatus by expansion of an associated member which substantially fills the uterine cavity, thus applying pressure to the material to force it into the Fallopian tubes. The material is initially introduced into the uterine cavity via a probe member inserted into the cavity.

It has been determined that there is a need to provide apparatus of this type having a disposable dispensing probe member and associated material transfer means. This and other features of the invention are described hereinbelow.

SUMMARY OF THE INVENTION

This invention is directed to improvements in apparatus for dispensing materials into the canals of the Fallopian tubes of female primates. More specifically, the invention is directed to introducing a disposable dispensing probe assembly and various operating features for improving the convenience of operation of such apparatus.

The primary details of the overall apparatus are described in the U.S. patents cited above which are incorporated by reference herein. That apparatus has an elongated dispensing probe having a forward end carrying an expandable balloon-like assembly. A dispensing housing having an actuator is used to expand the balloon assembly and to cause the discharge of the materials into the uterine cavity from the probe. The dispenser has a first drive assembly operable to initially partially expand the balloon-like assembly to form a seal and hold structure in the lower portion of the uterine cavity. Continued manipulation of the actuator causes discharge of the material into the uterine cavity above the partially expanded balloon-like assembly. As the actuator is further manipulated, the balloon assembly expands to substantially conform to and fully displace the uterine cavity and thus force the materials into the Fallopian tubes. The sequence of events is accomplished by actuation of a control actuator by an operator who moves the actuator between various positions.

The highly flexible balloon-like member not only conforms to the shape of the uterine cavity, but actually substantially fills the cavity and conforms to the shape of the individual isthmus of each Fallopian tube, thus effectively sealing the isthmus. By holding the control mechanism in the fully actuated position, the operator may seal the entrance to the Fallopian tubes for as long as necessary for the dispensed material to "set-up" within the Fallopian tubes. After the desired holding time, the operator may then manipulate the actuator control mechanism to deflate the balloon-like member and then may withdraw the probe portion of the device from the body.

More specifically, the invention provides an improved apparatus for dispensing material into the Fallopian tubes of a female primate, the apparatus including expandable means positionable in the uterine cavity and adapted to be enlarged to substantially fill the cavity, probe means carrying the expandable means at one end thereof and including first and second conduits, housing means carrying material dispensing control means and expansion control means, the latter means being operatively associated with the first of the probe conduits for operating the expandable means, the housing means being adapted to receive a container of the material to be dispensed and including means for transferring the material from the container to the second of the probe conduits for delivery of the material to the uterine cavity via the probe means, the transferring means being operatively associated with the material dispensing control means, the improvement comprising disposable probe means adapted for being selectively connected to the housing means and wherein the material transfer means is external to the housing means and extends externally of the housing means from an attachment point on the probe means to the ampule and dispensing control means.

The apparatus will preferably also include an open cradle for receiving the end portion of the external material transfer means and holding same in position for operative contact with the ampule by means of a locking arm carried by the housing.

The end of the needle is protected by a member impaled thereon which slides along the needle away from the end as the container is penetrated.

A hold-down button is also carried on the housing for fixing the control means in a predetermined position.

IN THE DRAWINGS

FIG. 1 is a pictorial view of the apparatus of the invention with some parts exploded;

FIG. 2 is a partial pictorial view of the apparatus with some parts of FIG. 1 assembled;

FIG. 3 is a partial pictorial view of the apparatus with parts of FIG. 1 further assembled;

FIG. 4 is a vertical sectional elevation taken along line 4—4 of FIG. 2 and slightly enlarged;

FIG. 5 is a partial plan view with parts cut away taken at 5 of FIG. 1, and

FIG. 6 is a vertical section with parts cut away, the section being taken along line 6—6 of FIG. 5 and slightly enlarged.

DESCRIPTION OF THE PREFERRED EMBODIMENT

Referring to the drawings, there is shown in FIG. 1 the improved dispensing apparatus of this invention, the apparatus having its disposable dispensing probe disconnected from the dispensing housing 12. Probe or tubular member 10 has a length sufficient to pass through the vaginal cavity and into the uterine cavity of a female primate. Member 10 has a longitudinal passage extending throughout its length. A balloon assembly, indicated generally at 14 is mounted on the upper or outer end of member 10. Balloon assembly 14 has a flexible and expandable sleeve member 16 surrounding the upper end of probe 10. Fasteners 18 and 20, such as a collar or the like, provide the attachment of sleeve or sheath 16 to probe 10. Probe 10 has a plurality of openings (not shown) which provide communication between the probe interior passage and a chamber within sleeve member 16. Sleeve member 16 may be a tubular sheet member of soft and relaxed, flexible and elastic material, such as rubber or plastic, that expands with minimum tension. Preferably, the material used for member 16 has a low surface tension which allows uniform expansion under relatively low pressure. Member 16 will thus expand to substantially fill a uterine cavity in which it is placed and conform to the shape of the cavity without applying extreme pressures to localized portions of the uterine walls. Through its extreme flexibility, member 16 will also expand into and conform to the shape of the isthmus at each Fallopian tube opening in the uterine cavity. This will substantially or effectively seal each isthmus.

The upper or outer end of probe 10 includes the terminal portion of an elongated tube 22 which is secured by a cyanoacrylic adhesive or the like to probe 10 at 24 and enters it to interiorly extend the length of probe 10. Tube 22 is hollow and acts as a conduit for carrying a set-table fluid-like material to the upper or outer end of probe 10 which in turn directs the material into the upper section of a uterine cavity into which probe 10 has been inserted. Two conduits are thereby provided in tube 10, a first conduit provided by probe 10 and a second conduit provided by tube 22 inside of probe 10. Tube 22 terminates at its other end in a sharp needle-like end 42 and a support member 44 which carries needle 42. The open end of needle 42 is covered and closed by means of a rubber or elastomer member 46.

Probe 10 is connected to housing 12 as shown in FIGS. 2 and 4 by means of an internally threaded female cap 26 which mates with an externally threaded male member 28 (seen in FIG. 4) extending from housing 12. Cap 26 includes a central opening 30 through which probe 10 extends to seat in an O-ring assembly 32 by means of a mating annular depression 34 on the end of the probe which snaps into the O-ring. The parts may be tapered relative to each other so as to insure for tight fit. By means of this connection to housing 12, probe 10 is enabled to function as a conduit for the supply and withdrawal of air to balloon assembly 14 through communication with the piston 36 and vented cylinder 38 assembly by means of conduit 40 within housing 12, details of which are shown in FIG. 4. Reference may be had to the aforementioned incorporated patents for additional detail.

Upon insertion of probe 10 through cap 26 and connection to housing 12, the end of tube 22 including support member 44, needle 42 and member 46 can be conveniently received onto housing 12 by cradle 48. Cradle 48 is shaped so as to provide a seat 50 for support member 44 and to allow needle 42 and sealing member 46 to extend rearwardly thereof. A locking arm 52 is rotatably carried on male member 28 between cap 26 and the end of housing 12 so as to be clamped therebetween in various selected positions by tightening cap 26 as shown in FIGS. 1 and 3. A fixed stop 53 may also be carried by housing 12. In FIG. 1 arm 52 is turned up and away from cradle 48. In FIG. 3, arm 52 is turned downwardly so as to rest against support member 44 to hold tube 22 and needle 42 in a fixed position in cradle 48.

Housing 12 is also adapted to include another cradle arrangement generally indicated at 54 which is shaped to receive a material or chemical container or ampule 56. Ampule 56 as fully described in the aforenoted incorporated patents includes a tubular container body 58, an end 60 adapted to receive and be punctured by needle 42 and an opposite end 62 adapted to be acted upon by a push rod member 64 carried by housing 12 which pushes end 62 into body 58 to force the contents of the ampule into tube 22 and out the end of probe 10 into the uterine cavity.

As shown, protective end member 46 is allowed to remain impaled needle 42 when ampule 56 is placed in cradle 54. Member 46 is merely pushed further onto needle 42 as ampule end 60 is forced against needle 42 by action of push rod 64 during operation of the device. This arrangement allows needle 42 to penetrate ampule 56 with minimal compromise of the sterility of the needle and to maintain tube 22 in a closed condition during insertion of probe 10 into the uterus thereby preventing entrance of any vaginal or other body fluids into probe 10.

As can be seen in FIGS. 1 and 2, a disposable probe 10 including tube 22 with protected sterile needle 42 is provided which is completely external to housing 12 and easily connected thereto and easily disconnected therefrom.

The device also includes a finger ring 66 which is connected to an elongated actuator assembly, generally indicated at 68 in FIG. 5, which is slidably received inside housing 12 as is fully described in the aforenoted and incorporated patents. The assembly is connected to piston 36 and to push rod 66 so as to enable them to be moved reciprocably within cylinder 38 and cradle 54, respectively, by reciprocably manipulating finger ring 66. Such an arrangement is described in some of the aforenoted and incorporated patents as a single stroke actuator arrangement.

More specifically, the single stroke actuator assembly 68 includes the following arrangement which is best seen in FIGS. 4, 5 and 6. As shown in FIG. 4, cylinder 38 includes an annular pressure release groove 70. A short cylinderical boss 72 extends inwardly from the center of wall 74. The inner end of probe 10 connects to boss 72 where air passage 40 is provided.

As previously noted, the actuator assembly 68 also includes a piston 36 slidably carried in cylinder 38. Piston 36 has a closed forward end or head which includes an open bore or recess 76 for accommodating boss 72 when piston 38 is in the full "in" position. The head of piston 36 also includes a peripheral outwardly open notch portion indicated at 78 accommodating a sealing or O-ring seal 80. Notch 78 on piston 36 is open to groove 70 and the piston includes a short radial vent passage (not shown) connecting base 76 to notch 78. Notch 78 and the radial vent passage thus provide an air passage between passage 40 and groove 70.

Referring now to FIG. 5, actuator assembly 68 has an elongated tubular body 82 slidably located within piston 38. As shown in FIGS. 5 and 6 a pair of ears 84 are connected to body 82 serving to interconnect it to push rod 64 whereby single action is obtained for movement of both piston 36 and push rod 64 by manipulation of finger ring 66. Movement of tubular body 12 inwardly carried the forward edges of ears 84 against shoulder 86 on push rod 64.

Actuator assembly 68 is movable with housing 12 to a first full "in" position close to the bottom of cylinder 38. In use, before an ampule has been placed in cradle 54, the actuator assembly is moved to the full "in" position by pushing finger ring 66 all the way into housing 12. This exposes push rod 64 placing it in cradle 54 as shown in FIG. 1 preventing the loading of an ampule into the apparatus. Any air trapped in sleeve 16 is vented or evacuated by means of the air passage formed between notch 78 and groove 70.

The actuator assembly is then retracted slightly from housing 12. This establishes a vacuum force on sleeve 16 collapsing it tightly against probe 10. The vacuum force is established because O-ring 80 moves out of groove 70 and into sealing engagement with the cylinder wall proper. The instrument is now ready for insertion of probe 10 into the vagina and uterine cavities. To facilitate handling of the instrument during this phase of the procedure, it has been equipped with a normally unlatched button 88 which may be depressed to a latched or locked position as shown in FIG. 6.

As seen in FIG. 66 button 88 is fitted with an upwardly biasing spring 90 which maintains it in its normal upward unlocked position. When actuator assembly 68 has been withdrawn partially to collapse sleeve 16, button 88 may be depressed so as to cause its bottom portion to be interposed between ears 84 and shoulder 86 to hold the actuator assembly in position by holding button 88 down. This facilitates handling of the instrument during insertion into the body and prevents the vacuum at sleeve 16 from drawing the actuator assembly to the full "in" position and accidentially venting the sleeve.

Once probe 10 is in the uterine cavity, button 88 is released and actuator assembly 68 is moved to its full "out" position by withdrawing finger ring 66. Piston 36 is moved outwardly in cylinder 38 locating O-ring 80 outwardly of a small vent hole (not shown) in the cylinder. Air then flows into cylinder chamber 38 through the hole. Push rod 64 is also retracted to a rearward position by this motion, clearing cradle 54 so that an ampule can be loaded therein.

Following loading of an ampule, actuator assembly 68 is pushed into housing 12. As it moves inwardly, sleeve 16 partially expands and ampule 56 is punctured causing the contents to be dispensed through tube 22 out of the end of probe 10 into the uterine cavity. Continued inward movement of the actuator assembly expands sleeve 16 further, pushing the dispensed materials into the Fallopian tubes.

Sleeve 16 is collapsed by partially withdrawing finger ring 66 from housing 12. This moves piston 36 outwardly to again form a vacuum which collapses the sleeve. Button 88 is pushed down and the instrument is removed from the body.

Having described the invention, the embodiments in which an exclusive property right is claimed are defined below.

What is claimed is:

1. In apparatus for dispensing material into the Fallopian tubes of a female primate, the apparatus including expandable means positionable in the uterine cavity and adapted to be enlarged to substantially fill the cavity, probe means carrying the expandable means at one end thereof and including first and second conduits, housing means carrying material dispensing control means and expansion control means, the latter means being operatively associated with the first of the probe conduits for operating the expandable means, the housing means being adapted to receive an ampule of the material to be dispensed and including means for transferring the material from the ampule to the second of the probe conduits for delivery of the material to the uterine cavity via the probe means, the transferring means being operatively associated with the material dispensing control means, the improvement comprising disposable probe means adapted for being selectively connected to the housing means and wherein the material transfer means is external to the housing means and extends externally of the housing means from an attachment point on the probe means to the ampule and the dispensing control means.

2. The apparatus of claim 1 wherein the housing means includes mounting means for receiving the end portion of the external material transfer means and positioning it for contact with an ampule carried by the housing.

3. The apparatus of claim 2 wherein the housing means includes locking means for locking the end portion of the transfer means in the mounting means.

4. The apparatus of claim 2 wherein the end portion of the transfer means and the mounting means are shaped for mutual interfitting relationship.

5. The apparatus of claim 4 wherein the mounting means includes an open cradle for receiving the end portion of the external material transfer means and holding same in position for operative contact with the ampule.

6. The apparatus of claim 5 wherein the housing means includes locking means for locking the end portion of the transfer means in the mounting means.

7. The apparatus of claim 6 wherein the locking means comprises a locking arm carried by the housing means.

8. The apparatus of claim 7 wherein the locking arm is rotatably mounted on the housing means and the apparatus includes an end cap engaging the housing means for clamping the locking arm between the end cap and the housing means such that it may be selectively moved between a plurality of fixed positions.

9. The apparatus of claim 8 wherein the end cap is adapted for affixing the probe to the housing means.

10. The apparatus of claim 1 wherein the end of the external material transfer means terminates in a needle and the needle carries a covering member impaled on the end thereof and capable of being moved on the needle away from the end thereof when penetration of the ampule is accomplished.

11. The apparatus of claim 1 including latch means carried by the housing for latching the material dispensing control means and the expansion control means in a predetermined position.

12. The apparatus of claim 11 including means biasing the latch means to a predetermined position.

13. The apparatus of claim 11 including means biasing the latch means to a normally unlatched position.

14. An elongated disposable dispensing probe for dispensing material into the Fallopian tubes of a female primate, the probe carrying expandable means and dispensing orifice means near one end thereof, the other end of the probe being adapted for selective connection to a dispensing housing, first conduit means included in the probe and communicating with the housing and the expandable means for operating it, second conduit means included in the probe for transferring material to be dispensed to dispensing orifice means at the one end of the probe and external material transfer means for transferring material to be dispensed from the housing to the second conduit means, the external transfer means being connected by one end thereof to the probe and second conduit means thereof at a point intermediate the ends of the probe, the other end of the transfer means terminating in a hollow needle and thereby being adapted for selective connection to material source means carried by the housing.

15. The disposable probe of claim 14 wherein the expandable means comprises a balloon.

16. The disposable probe of claim 14 wherein the second conduit and the external transfer means comprise a continouous length of tubing.

17. The disposable probe of claim 14 wherein the needle carries an impaled body-end member for closing the end of the needle.

* * * * *